(12) United States Patent
Mills et al.

(10) Patent No.: US 8,790,930 B2
(45) Date of Patent: Jul. 29, 2014

(54) INTELLIGENT PIGMENTS AND PLASTICS

(75) Inventors: Andrew Mills, Belfast (GB); Pauline Grosshans, Glasgow (GB); Graham Skinner, Glasgow (GB)

(73) Assignee: University of Strathclyde, Glasgow (GB)

( * ) Notice: Subject to any disclaimer, the term of this patent is extended or adjusted under 35 U.S.C. 154(b) by 67 days.

(21) Appl. No.: 13/502,268

(22) PCT Filed: Oct. 14, 2010

(86) PCT No.: PCT/GB2010/001915
§ 371 (c)(1),
(2), (4) Date: Jul. 19, 2012

(87) PCT Pub. No.: WO2011/045572
PCT Pub. Date: Apr. 21, 2011

(65) Prior Publication Data
US 2012/0276647 A1    Nov. 1, 2012

(30) Foreign Application Priority Data
Oct. 16, 2009    (GB) .................................. 0918212.2

(51) Int. Cl.
*G01N 21/77* (2006.01)
*G01N 21/78* (2006.01)
*G01N 21/76* (2006.01)

(52) U.S. Cl.
USPC ........... 436/113; 436/133; 436/136; 436/164; 436/166; 436/167; 436/172; 422/400; 422/86; 422/88

(58) Field of Classification Search
USPC ......... 436/113, 127, 133, 136, 138, 164, 166, 436/167, 172; 422/400, 68.1, 83, 86, 88
See application file for complete search history.

(56) References Cited

U.S. PATENT DOCUMENTS

| | | | | |
|---|---|---|---|---|
| 4,421,719 | A * | 12/1983 | Burleigh | 422/416 |
| 5,114,676 | A * | 5/1992 | Leiner et al. | 422/82.06 |
| 5,472,668 | A * | 12/1995 | Mills et al. | 422/425 |
| 5,480,611 | A * | 1/1996 | Mills et al. | 422/425 |
| 5,484,454 | A | 1/1996 | Furhmann et al. | |
| 5,567,598 | A * | 10/1996 | Stitt et al. | 435/29 |
| 5,849,594 | A * | 12/1998 | Balderson et al. | 436/133 |
| 6,015,715 | A | 1/2000 | Kirschner et al. | |
| 6,149,952 | A * | 11/2000 | Horan | 426/87 |
| 6,395,506 | B1 * | 5/2002 | Pitner et al. | 435/32 |
| 6,531,097 | B1 * | 3/2003 | Vojnovic et al. | 422/82.07 |
| 6,989,246 | B2 * | 1/2006 | Yeh | 435/34 |
| 2005/0037512 | A1 * | 2/2005 | Yeh et al. | 436/166 |

FOREIGN PATENT DOCUMENTS

| | | |
|---|---|---|
| EP | 0 449 017 A | 10/1991 |
| EP | 1 327 874 A | 7/2003 |
| JP | 6-43155 A | 2/1994 |
| JP | 6-82100 B2 | 10/1994 |
| JP | 11-505923 A | 5/1999 |
| JP | 2002-529682 A | 9/2002 |
| JP | 2003-362628 A | 9/2003 |
| JP | 2006-308423 A | 11/2006 |
| WO | WO 2004/059281 A2 | 7/2004 |
| WO | WO 2005/049198 A1 | 6/2005 |

OTHER PUBLICATIONS

Lee et al. Chemical Communication, 2004, pp. 1912-1913.*
Mills, Andrew. Chem. Soc. Rev., vol. 34, 2005, pp. 1003-1011.*
Combined Search Report and Examination Report for Application No. GB1017340.9 dated Jan. 27, 2011.
Mills, A., et al.; "*Hydrogen peroxide vapour indicator*;" Sensors and Actuators B: Chemical, vol. 136, No. 2; pp. 458-463; dated Mar. 2009; Abstract retrieved on Mar. 14, 2014 from <http://www.sciencedirect.com/science/article/pii/S0925400508008605>.
Mills, A., et al.; "*Nanocrystalline SnO2-based, UVB-activated, colourimetric oxygen indicator*;" Sensors and Actuators B: Chemical, vol. 136, No. 2; pp. 344-349; dated Mar. 2009; abstract retrieved on Mar. 14, 2014 from <http://www.sciencedirect.com/science/article/pii/S0925400508008691>.
International Preliminary Report on Patentability for Application No. PCT/GB2010/001915; dated Apr. 17, 2012.
International Search Report and Written Opinion for Application No. PCT/GB2010/001915; dated May 4, 2011.
Office Action for Japanese Application No. 2012-533687; dated Jan. 21, 2014.
Office Action for Chinese Application No. 201080057003.9 dated Mar. 17, 2014.
Lee, S-K. et al., *Novel UV-Activated Colorimetric Oxygen Indicator*, Chem. Mater. 17 (2005) 2744-2751.

* cited by examiner

*Primary Examiner* — Maureen Wallenhorst
(74) *Attorney, Agent, or Firm* — Alston & Bird LLP

(57) ABSTRACT

A chemical indicator having a particulate inorganic substrate, and at least one reactive dye or ink coated on and/or impregnated within the particulate inorganic substrate. Coating and/or impregnating at least one reactive dye or ink on or within a particulate inorganic substrate improves the storage stability and/or thermal stability of the at least one reactive dye or ink, which typically includes relatively unstable compounds. This allows the present indicators to be incorporated into thermoplastic polymer materials and processed conventionally while maintaining the efficacy and stability of the new indicators. The indicators provide simple, reliable, and cost effective detection means for detecting analytes such as ammonia, carbon dioxide, and oxygen, and may find use in applications such as food packaging and medical applications.

28 Claims, 11 Drawing Sheets

| Dye | Abbreviation |
|---|---|
| m-Cresol Purple | MCP |
| Phenolphthalein | - |
| Phenol Red | PR |
| Cresol Red | CR |
| o-cresolphthalein | - |
| Thymolphthalein | - |
| Thymol blue | TB |
| Naphthol blue black | - |

Figure 1

| Dye | Abbreviation | Dye family |
|---|---|---|
| Bromophenol Blue | BPB | Hydroxy triarylmethane |
| Bromocresol Green | BCG | Hydroxy triarylmethane |
| Bromocresol Purple | BCP | Hydroxy triarylmethane |
| Bromothymol Blue | BTB | Hydroxy triarylmethane |
| Phloxine Blue | PB | Fluorone (fluorescin derivative) |
| Thymol Blue | TB | Hydroxy triarylmethane |
| m-Cresol Purple | MCP | Hydroxy triarylmethane |

Figure 2

| Dye | Abbreviation | Dye family |
|---|---|---|
| Methylene blue, | MB | Thiazine |
| Thionine | Th | Thiazine |
| Azure B | AzB | Thiazine |
| Nile blue | NR | Oxazine |
| Ruthenium tris bypyridyl | Rubpp | metal complex |
| Tris(4,7-diphenyl-1,10-phenanthroline) ruthenium (II) perchlorate | Rudpp | metal complex |
| Platinum (II) octaethyl porphyrin ketone | PtOEPK | metal complex |
| Proflavin | Pf | proflavin |

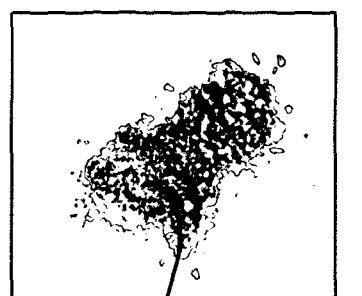 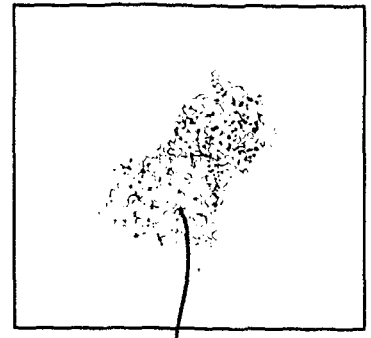
Figure 11
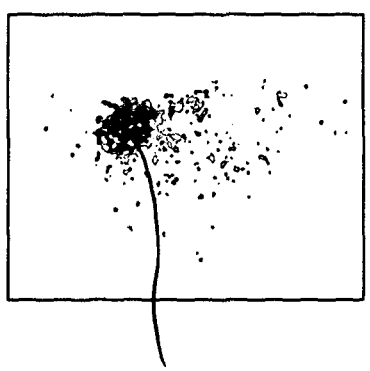 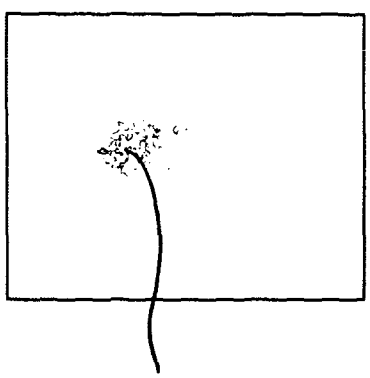
Figure 12

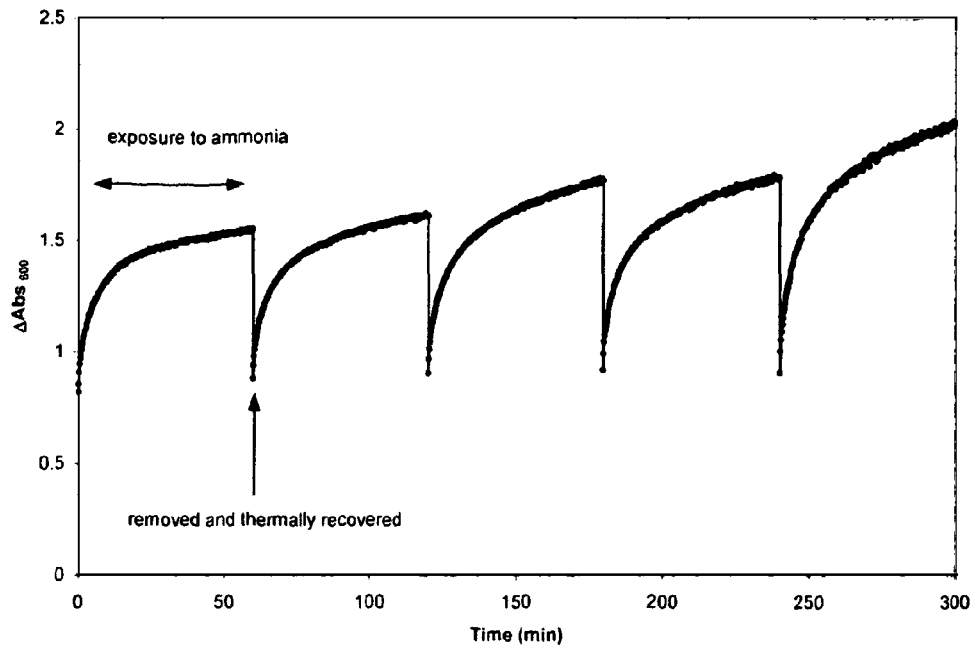

Figure 19

| Dye | pKa | Colour before exposure | Colour after exposure | Response | Ambient Recovery |
|---|---|---|---|---|---|
| BPB | 4.10 | Yellow/orange | Blue | Good, very distinct colour change | Slow |
| BCG | 4.90 | Orange | Green/Blue | Good colour change | Moderate |
| BCP | 6.8 | Orange | Green | Moderate | Moderate |
| BTB | 7.0 | Yellow/orange | Dark yellow | Poor | Quick |
| PB | unknown | Colourless/pale pink | Bright Pink | Good, very distinct colour change | Very Slow |
| TB | 1.65 | Pink/Purple | Yellow/Pink | Moderate | Slow |
| MCP | 1.6 | Pink/Purple | Yellow/Pink | Moderate | Slow |

Figure 20

INTELLIGENT PIGMENTS AND PLASTICS

FIELD OF INVENTION

The present invention relates to chemical indicators comprising a particulate inorganic substrate; and at least one reactive dye or ink coated on or impregnated within the particulate inorganic substrate.

The present invention also relates to a method of preparing such chemical indicators comprising providing a particulate inorganic substrate with at least one reactive dye or ink.

The present invention also relates to a polymer composite comprising at least one polymer, and one or more such chemical indicators.

The present intention also relates to a method of preparing such a polymer composite, comprising providing at least one polymer with one or more such chemical indicators.

The present invention also relates to the use of such a polymer composite in food packaging and/or medicine, e.g., respiratory medicine.

BACKGROUND TO INVENTION

Colorimetric indicators are a well-known means of detecting the presence of a chemical substance in a particular medium. This type of indicator includes, e.g., pH indicators which exhibit a colour change as the pH of the medium in which it is placed varies.

Such indicators rely on the optical properties of reactive dyes or inks. These dyes can exist in at least two different chemical states, with each form of the dye absorbing light in a particular range of wavelength. When such a reactive dye existing in a first form is exposed to a given substance, it reacts with the substance via a reversible chemical reaction, thereby turning into a second form of the dye. As the second form of the dye absorbs light at a different wavelength, the chemical reaction provides a colour change which is visible by an observer.

The use of colorimetric indicators thus potentially provides an attractive solution to the problem of detecting the presence of some particular chemical substances.

Such substances include gases, such as carbon dioxide, ammonia, and oxygen which have particular significance in, amongst other things, food packaging.

Detection of carbon dioxide has always had significance due to the negative effect of carbon dioxide on health if held in too high concentrations. In medicine, carbon dioxide is one of the key, basic analytes that are routinely monitored in the blood of hospital patients. Capnography is an area in medicine wholly devoted to the monitoring of levels of carbon dioxide in breath. Not only does the presence of carbon dioxide provide important valued medical information, but also its temporal variations in the exhaled breath is used routinely to provide diagnostic information via capnography. In anaesthesiology, one method to ensure the correct placement of the tube carrying the gases to the lungs into the trachea, rather than the oesophagus, is to monitor the level of carbon dioxide (typically 4-5% in exhaled breath).

In the food industry, the use of modified atmosphere packaging (MAP) is well established. MAP packaging involves flushing food with an oxygen-free gas, usually carbon dioxide, and sealing, ready for distribution to the wholesale and/or retail trader. The purpose of MAP packaging is to prevent aerobic spoilage microbe growth, and usually allows food to stay fresh 3-4 times longer. Detection of levels of carbon dioxide in MAP-packaged food is essential to indicate the freshness of the food.

Ammonia ($NH_3$) is a caustic, hazardous gas with a pungent characteristic odour. It is widely used both directly and indirectly in the production of explosives, fertilisers, pharmaceuticals, household cleaning products and as an industrial coolant. Ammonia and other volatile amines also give spoiled fish its 'off' taste and smell, as these are produced as fish meat decays. As a result there is a need to monitor ammonia levels not only in industry to monitor for leaks and waste water effluents, but also in the food packing industry, in particular for fish packaging. After fish are caught and killed microorganisms form on the skin and scales. These are known as specific spoilage organisms (SSO) which produce ammonia and volatile amines including trimethylamine (TMA) and dimethylamine (DMA) from the amino acids present in the fish. These microbial degradation products are collectively known at total volatile basic nitrogen (TVB-N). By measuring the TVB-N if would be possible to give a measure of how fresh the fish is.

The main cause of most food spoilage is oxygen, because its presence allows a myriad of aerobic food-spoiling microorganisms to grow and thrive. Oxygen also spoils many foods through enzyme-catalysed reactions, as in the browning of fruit and vegetables, destruction of ascorbic acid and the oxidation of a wide range of flavours. Many oxidative food-spoiling reactions, including lipid oxidation, occur non-enzymically.

A number of colorimetric indicators capable of detecting the presence of particular analytes have been reported in the literature. The reactive dyes employed in such indicators typically have poor thermal stability and/or shelf life, therefore rendering their commercialisation and utilisation in finished articles difficult. For instance, the use of colorimetric $CO_2$ detectors in respiratory medicine has been reported. Examples of such commercial devices include, e.g., Pedi-Cap (Nellcor, Pleasanton, Calif.) and Mini $StatCO_2$ (Mercury Medical, Clearwater, Fla.). However, once removed from their sealed packaging, the average life span under normal atmosphere of such indicators is very short, typically approximately 2 hours for Pedi-Cap, and approximately 24 hours for Mini $StatCO_2$.

In the case of carbon dioxide, solvent based solid, dry carbon dioxide sensors were made possible with the discovery that a phase transfer agent, PTA, is able to extract the anionic form of the colorimetric pH indicator, from the highly polar protic medium into the less polar environment of the polymer/plasticizer. The water associated with the dye is also delivered to the hydrophobic polymer via the PTA. In such plastic thin $CO_2$ film sensors, the equilibrium set up between the dye and carbon dioxide can be represented by the following reaction:

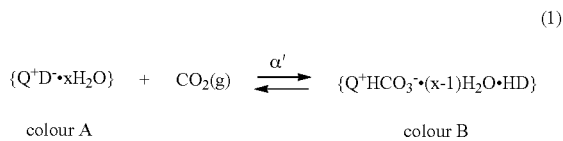

$$\{Q^+D^- \cdot xH_2O\} + CO_2(g) \xrightleftharpoons{\alpha'} \{Q^+HCO_3^- \cdot (x-1)H_2O \cdot HD\} \quad (1)$$

colour A  colour B

Where $\alpha'$ is the equilibrium constant associated with the process. Despite the importance of $CO_2$ as an analyte and the significant interest in $CO_2$ indicators, few colour-based $CO_2$ indicators have been commercialised. One of the reasons for this is the poor stability over time of such indicators. Most have shelf lives of less than six months under ambient air conditions due to, amongst other things, a poor thermal stability of the phase transfer agents used and a tendency to react irreversibly with other acid gases such as $NO_2$ and $SO_2$.

Therefore, there is a need in the prior art to develop new chemical indicators, and in particular colorimetric indicators, to provide simple, reliable, and cost effective detection means that exhibit improved storage and thermal stability.

Further, there is a need in the prior art to develop new polymer-based compositions incorporating such indicators, which compositions may be prepared and processed via known polymer processing techniques while maintaining the efficacy and stability of the new indicators.

SUMMARY OF INVENTION

According to an aspect of the present invention there is provided a chemical indicator comprising a particulate inorganic substrate, and at least one reactive dye or ink coated on and/or impregnated within the particulate inorganic substrate.

By such provision the storage stability and/or thermal stability of the at least one reactive dye or ink may be improved.

A particulate inorganic substrate is understood to be defined as a substrate which is typically made of an insoluble material, and which is provided in a particulate form. This typically includes e.g. inorganic fillers and/or inorganic pigments, which may be white, transparent, or coloured. In the context of the invention an insoluble material is understood to be defined as a material that is insoluble in a water-based or organic solvent in which the at least one reactive dye or ink is intended to be dissolved, prior to coating and/or impregnating within the particulate inorganic substrate.

Thus, it is to be understood that the present invention does not relate to, e.g., inks coated on macroscopic inorganic substrates such as metal sheets for use as, e.g., drinks cans.

A reactive dye or ink is understood to be defined as a dye that can exist in at least two different chemical states, with each form of the dye absorbing light in a particular range of wavelength. When such dyes are exposed to a given substance, they can reversibly or irreversibly react from a first chemical state into a second chemical state, thereby inducing a visible colour change.

Advantageously, the chemical indicator may have high thermal stability, e.g. at least approximately 80° C., preferably at least 110° C.

Beneficially, the chemical indicator may have long storage stability under dark, but otherwise ambient conditions, e.g. at least one week, preferably at least one month, more preferably at least six months, most preferably at least twelve months.

Preferably, the indicator may be a colorimetric or luminescence-based indicator.

Conveniently, the particulate inorganic substrate may be in powder form.

Typically, the particulate inorganic substrate may be an inorganic pigment, e.g. silica, titania, alumina, magnesium oxide, calcium oxide or a zeolite, especially silica.

In one embodiment, the particulate inorganic substrate may be hydrophobic, e.g. hydrophobic silica or hydrophobic alumina.

The term hydrophobic it is understood to mean either inherently hydrophobic, or hydrophobised, i.e. a substrate which has been modified, e.g. surface-modified, to render the substrate hydrophobic, e.g. by incorporating hydrophobic chemical groups on the surface of the substrate.

In another embodiment, the particulate inorganic substrate may be hydrophilic, e.g. hydrophilic silica or hydrophilic alumina.

The term hydrophilic it is understood to mean either inherently hydrophilic, or hydrophilised, i.e. a substrate which has been modified, e.g. surface-modified, to render the substrate hydrophilic, e.g. by incorporating hydrophilic chemical groups on the surface of the substrate.

In yet another embodiment, the particulate inorganic substrate may be an untreated particulate inorganic substrate, e.g. untreated titania. By such provision the particulate inorganic substrate, e.g. titania, may retain its photocatalytic properties.

Typically, the at least one reactive dye may be capable of reacting to the presence of at least one chemical substance to be detected.

Typically, the chemical substance to be detected may be a chemical species capable of causing a chemical change in the reactive dye.

The chemical substance may be present in the air and may itself be gaseous species, e.g. carbon dioxide, ammonia or oxygen. Alternatively, the chemical substance may be a particulate material or may be in solution or suspension, for example in water. The chemical may itself be a liquid such as an alcohol, solvent or the like.

Typically also, the at least one reactive dye may be in equilibrium between at least two chemical forms or states.

Conveniently, the at least one reactive dye may exhibit a first colour in a first chemical form or state, and a second colour in a second chemical form or state.

Preferably, the first and second colours may be different.

In one embodiment, the at least one reactive dye may be a carbon dioxide-sensitive reactive dye such as m-Cresol Purple (MCP, Hydroxy triarylmethane), Thymolphthalein (3,3-bis(4-hydroxy-2-methyl-5-propan-2-ylphenyl)-2-benzofuran-1-one), o-Cresolphthalein, Acryloly florescein (AcFl), β-methyl umbelliferon (BMUB), Bromothymol blue (BTB, Hydroxy triarylmethane), 5' and 6'-Carboxyseminaphtholfluorescein (c-SNAFL), 5' and 6'-Carboxyseminaphthol-rhodamine (c-SNARF), Cresol Red (CR, o-Cresolsulfonephthalein), Hexadecyl trimethyl ammonium cation ($CTA^+$), Hexadecyl trimethyl ammonium hydroxide (CTAH), Dual lumophore referencing (DLR), 2-(2,4-Dinitrophenylaxo)-1-naphthol-3,6disulphonic acid (DNPA), tris(thenoyltrifluoroacetonato) europium (III) ($[Eu(tta)_3]$), Fluorescein (Fl, resorcinolphthalein), 7-hydroxycoumarin-4-acetic acid (HCA), 1, Hydroxypyrene-3,6,8-trisulphonic acid (HPTS), Neutral red (NR, toluoylene red), Phenol Red (PR, phenolsulfonphthalein), Rhodamine 6G (R6G), Sulforhodamine 101 (SRh), Thymol blue (TB, thymolsulphonephthalein), Texas Red hydrazine (THR). It is to be understood that any other pH-sensitive dye or ink may be suitable for use as a $CO_2$-sensitive reactive dye.

In another embodiment, the at least one reactive dye may be an ammonia-sensitive reactive dye such as Bromophenol Blue (BPB, Hydroxy triarylmethane), Bromocresol Green (BCG, Hydroxy triarylmethane), Bromocresol Purple (BCP, Hydroxy triarylmethane), Bromothymol Blue (BTB, Hydroxy triarylmethane), Phloxine Blue (PB, Fluorone), Thymol Blue (TB, Hydroxy triarylmethane), or m-Cresol Purple (MCP, Hydroxy triarylmethane).

In another embodiment, the at least one reactive dye may be an oxygen-sensitive reactive dye. The indicator comprising the at least one oxygen-sensitive reactive dye may be a colorimetric indicator or a luminescence-based indicator.

The at least one oxygen-sensitive reactive dye may be, e.g. Methylene blue (MB, thiazine), Thionine (Th, thiazine), Azure B (AzB, thiazine), Nile blue (NR, oxazine), or any other dye which, upon reduction, is rendered oxygen-sensitive. This reduction may be effected photochemically, using a semiconductor photocatalyst such as titania, or chemically using a reducing agent such as ascorbic acid. The reactive dye may also be a dye which exhibits a fluorescence that is quenched by oxygen, such as Ruthenium tris bypyridyl (Rubpp, metal complex), tris(4,7-diphenyl-1,10-phenanthroline) ruthenium (II) perchlorate (Rudpp, metal complex), Platinum (II) octaethyl porphyrin ketone (PtOEPK, metal complex), Proflavin (Pf, proflavin).

In one embodiment, the chemical indicator may comprise more than one type of reactive dye. By such provision, the chemical indicator may be capable of detecting the presence of more than one analyte, and/or be capable or detecting changes in the concentration of a particular analyte, e.g. by providing reactive dyes that change colour at different concentrations of a particular analyte.

According to another aspect of the present invention there is provided a method of preparing a chemical indicator, comprising dissolving at least one reactive dye or ink in at least one solvent, mixing this with a particulate inorganic substrate, and evaporating the at least one solvent so as to form a particulate inorganic substrate comprising at least one reactive dye or ink coated and/or impregnated therein.

It is understood that the at least one solvent is generally capable of dissolving the at least one reactive dye or ink, but not the particulate inorganic substrate that is typically made of an insoluble material. The particulate inorganic substrate typically includes e.g. inorganic fillers and/or inorganic pigments, which may be white, transparent, or coloured.

Preferably, the method may comprise providing the particulate inorganic substrate in powder form.

Typically, the method may further comprise agitation and/or sonication.

Preferably, the at least one solvent may be an organic solvent, e.g. methanol. In such instance, the at least one reactive dye or ink may typically be a solvent-soluble dye.

Alternatively, at least one of the at least one solvent may comprise, e.g., water. In such instance, the at least one reactive dye or ink may typically be a water-soluble dye.

Typically, the chemical indicator may be a chemical indicator as described in a previous aspect of the invention.

According to another aspect of the present invention there is provided a polymer composite comprising at least one thermoplastic polymer, and at least one chemical indicator comprising a particulate inorganic substrate, and at least one reactive dye or ink coated on and/or impregnated within the particulate inorganic substrate.

The at least one chemical indicator may comprise a chemical indicator as described in relation to a previous aspect of the invention and embodiments associated therewith.

Advantageously, the at least one chemical indicator may have high thermal stability, e.g. at least approximately 80° C., preferably at least 110° C. By such provision the polymer composite may exhibit excellent sensing abilities even after exposure to relatively high temperatures applied during processing and/or fabrication, e.g. through extruding, calendering, and/or moulding.

Beneficially, the chemical indicator may have long storage stability under dark, but otherwise ambient conditions, e.g. at least one week, preferably at least one month, more preferably at least six months, most preferably at least twelve months.

Typically, the at least one chemical indicator may be dispersed in the at least one polymer.

Advantageously, the at least one chemical indicator may be substantially uniformly dispersed in the at least one polymer.

The polymer composite may comprise a melt-processed polymer composite, preferably extruded, and may be provided in the form of e.g. a film, sheet, tube, or any other suitable profile.

Preferably, the at least one thermoplastic polymer may comprise an addition polymer such as a polyolefin, e.g. polyethylene or polypropylene, or another thermoplastic addition polymer, e.g. polystyrene or a polyacrylate.

Alternatively, the at least one thermoplastic polymer may comprise a condensation polymer, e.g. polycarbonate, polyether, polyester, polyamide or polyacetal.

In one embodiment, the at least one thermoplastic polymer may be a hydrophobic polymer, e.g. polyethylene. In such instance, the at least one chemical indicator may comprise a hydrophobic particulate inorganic substrate, e.g. hydrophobic silica or hydrophobic alumina. By such provision the compatibility between the at least one chemical indicator and the at least one hydrophobic polymer in which it is dispersed may be improved. Alternatively, the at least one chemical indicator may comprise an untreated particulate inorganic substrate, e.g. untreated titania.

In another embodiment, the at least one thermoplastic polymer may be a hydrophilic polymer, e.g. polyethylene oxide. In such instance, the at least one chemical indicator may comprise a hydrophilic particulate inorganic substrate, e.g. hydrophilic silica or hydrophilic alumina. By such provision the compatibility between the at least one chemical indicator and the at least one hydrophilic polymer in which it is dispersed may be improved. Alternatively, the at least one chemical indicator may comprise an untreated particulate inorganic substrate, e.g. untreated titania.

In one embodiment, the polymer composite may comprise more than one type of chemical indicator. By such provision, the polymer composite may be capable of detecting more than one analyte and/or be capable or detecting changes in the concentration of a particular analyte, e.g. by providing chemical indicators that change colour at different concentrations of a particular analyte.

According to another aspect of the present invention there is provided a method of manufacturing a polymer composite, comprising providing at least one thermoplastic polymer with at least one chemical indicator as described in relation to a previous aspect of the invention and embodiments associated therewith.

The method may comprise mixing the at least one thermoplastic polymer and the at least one chemical indicator in comminuted form, e.g. powder.

The method may further comprise grinding the at least one thermoplastic polymer and the at least one chemical indicator together.

Preferably, the method may comprise dispersing the at least one chemical indicator in the at least one thermoplastic polymer, e.g. by melting.

Typically, the method may comprise the step of fabricating the polymer composite, comprising e.g. melt-processing the polymer composite.

Preferably, the fabricating step may comprise extruding or moulding the polymer composite into e.g. a film, sheet, tube, or another suitable profile.

The step of dispersing the at least one chemical indicator in the at least one thermoplastic polymer, e.g. by melting, may be carried out before the fabricating step.

Alternatively, the step of dispersing the at least one chemical indicator in the at least one thermoplastic polymer may be carried out during the fabricating step.

In one embodiment, the method may comprise blending a plurality of polymer composites prior to or during fabrication, each polymer composite being capable of detecting the presence of one or more selected analytes. The method may comprise blending, e.g., a first polymer composite comprising a first chemical indicator capable of detecting a first analyte, and a second polymer composite comprising a second chemical indicator capable of detecting a second analyte.

According to another aspect of the present invention there is provided the use of a polymer composite according to a previous aspect of the invention and embodiments associated therewith, in food packaging and/or medicine, e.g., respiratory medicine.

According to another aspect of the present invention there is provided an item of food packaging comprising at least one polymer composite according to a previous aspect of the invention and embodiments associated therewith.

The item of food packaging may be a closed item, e.g. a box, or an open item, e.g. a tray.

Alternatively, the item of food packaging may be a shapeless or flexible item of packaging, e.g. a wrapping film such as plastic wrap or cling film.

In one embodiment, the item of food packaging may comprise a plurality of distinct portions each comprising at least one polymer composite capable of detecting the presence of one or more selected analytes. The item of food packaging may comprise at least a first portion made from a first polymer composite comprising a first chemical indicator capable of detecting a first analyte, e.g. ammonia, and a second portion made from a second polymer composite comprising a second chemical indicator capable of detecting a second analyte, e.g. carbon dioxide, oxygen, or any other suitable analyte.

In one embodiment, each portion capable of detecting the presence of one or more selected analytes may be provided in a form such as to be capable or revealing information, e.g. a word or a symbol, upon colour change. The each portion may be capable of revealing a message or word, e.g. "danger" or "unsafe", when the release of a first analyte, e.g. ammonia, causes a change in colour of a first chemical indicator. Alternatively, a message or word, e.g. "safe", may be visible in the each portion in the absence of a first analyte, e.g. ammonia, and may disappear when the release of the first analyte causes a change in colour of a first chemical indicator.

According to another aspect of the present invention there is provided a medical device comprising a polymer composite according to a previous aspect of the invention and embodiments associated therewith.

In one embodiment, the medical device may be used in respiratory medicine.

The device may be in the form of, e.g., a tube, such as a respiratory tube.

By such provision the tube itself may be capable of detecting the presence of an analyte, e.g., carbon dioxide, thus avoiding the need to adapt a separate sensor or indicator onto the existing tubing assembly. This may not only improve the simplicity and ease of handling of the tubing assembly, but also avoid the risk of leakage and/or contamination arising from the presence of additional parts being connected to the main tube.

In one embodiment, the medical device may comprise a plurality of distinct portions each comprising at least one polymer composite capable of detecting the presence of one or more selected analytes. The medical device may comprise, e.g., a first portion made from a first polymer composite comprising a first chemical indicator capable of detecting a first analyte, e.g. carbon dioxide, and a second portion made from a second polymer composite comprising a second chemical indicator capable of detecting a second analyte.

In one embodiment, each portion capable of detecting the presence of one or more selected analytes may be provided in a form such as to be capable or revealing information, e.g. a word or a symbol, upon colour change. The each portion may be capable of revealing a message or word, e.g. "danger" or "unsafe", when the release of a first analyte, e.g. carbon dioxide, causes a change in colour of a first chemical indicator. Alternatively, a message or word, e.g. "safe", may be visible in the each portion in the absence of a first analyte, e.g. carbon dioxide, and may disappear when the release of the first analyte causes a change in colour of a first chemical indicator.

According to another aspect of the present invention there is provided a carbon dioxide sensor or indicator comprising a polymer composite according to a previous aspect of the invention and embodiments associated therewith, wherein the polymer composite comprises at least one chemical indicator comprising at least one carbon dioxide-sensitive reactive dye.

In one embodiment, the at least one carbon dioxide-sensitive reactive dye may comprise m-Cresol purple.

In one embodiment, the polymer composite may comprise at least one thermoplastic polymer which may comprise a polyolefin, e.g. polyethylene.

According to another aspect of the present invention there is provided an ammonia sensor or indicator comprising a polymer composite according to a previous aspect of the invention and embodiments associated therewith, wherein the polymer composite comprises at least one chemical indicator comprising at least one ammonia-sensitive reactive dye.

In one embodiment, the at least one ammonia-sensitive reactive dye may comprise Bromophenol blue.

In one embodiment, the polymer composite may comprise at least one thermoplastic polymer which may comprise a polyolefin, e.g. polyethylene.

According to another aspect of the present invention there is provided an oxygen sensor or indicator comprising a polymer composite according to a previous aspect of the invention and embodiments associated therewith, wherein the polymer composite comprises at least one chemical indicator comprising at least one oxygen-sensitive reactive dye.

In one embodiment, the at least one oxygen-sensitive reactive dye may comprise a colorimetric-based dye such as Methylene blue.

In another embodiment, the at least one oxygen-sensitive reactive dye may comprise a luminescence-based dye such as Rudpp.

In one embodiment, the polymer composite may comprise at least one thermoplastic polymer which may comprise a polyolefin, e.g. polyethylene.

BRIEF DESCRIPTION OF DRAWINGS

Embodiments of the invention will now be given by way of example only, and with reference to the accompanying drawings, which are:

FIG. 1 A table showing the types of $CO_2$-sensitive reactive dyes used in the preparation of chemical indicators according to a first embodiment of an aspect of the present invention;

FIG. 2 A table showing the types of ammonia-sensitive reactive dyes used in the preparation of chemical indicators according to a second embodiment of an aspect of the present invention;

FIG. 3 A table showing the types of oxygen-sensitive reactive dyes used in the preparation of chemical indicators according to a third embodiment of an aspect of the present invention;

FIG. 11 A photograph showing the colour change of oxygen-sensitive indicators according to a third embodiment of an aspect of the present invention when activated with UV light and then exposed to oxygen, using MB as reactive dye in a solvent-based $TiO_2$ pigment;

FIG. 12 A photograph showing the colour change of oxygen-sensitive indicators according to a third embodiment of an aspect of the present invention when activated with UV light and then exposed to oxygen, using MB as reactive dye in a water-based $TiO_2$ pigment;

FIG. 19 An absorbance response at 600 nm of a of the ammonia-sensitive polymer composite film of FIG. 16, showing five cycles of response to 1000 ppm ammonia for 1 hour followed by thermal recovery for 2 hours at 70° C.;

FIG. 20 A table showing a comparison of the response and recovery of ammonia-sensitive polymer composite films according to a second embodiment of an aspect of the present invention, using the reactive dyes of FIG. 2;

EXAMPLES

Preparation

Figure 4:
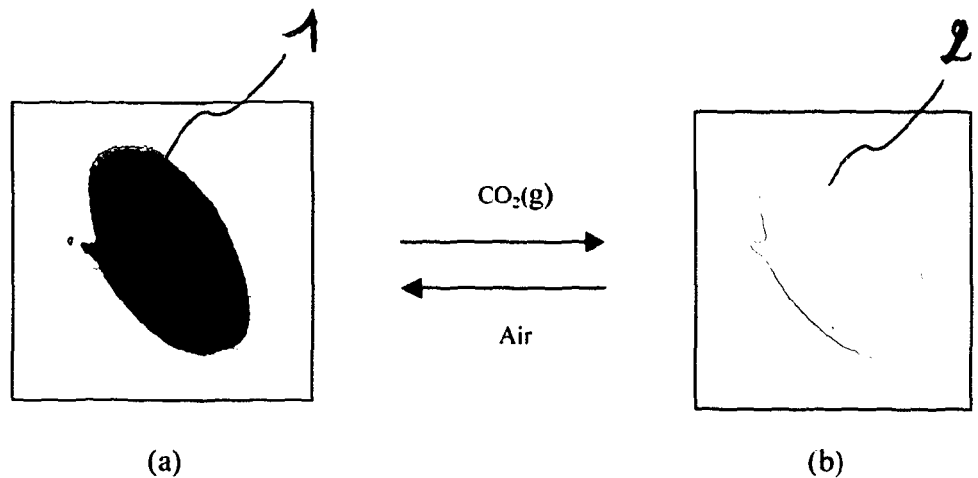
FIG. 4 A photograph showing the colour change of $CO_2$-sensitive indicators according to a first embodiment of an aspect of the present invention when exposed to $CO_2$, using MCP as reactive dye.

Silica (silicon dioxide) and alumina (aluminium oxide) were chosen as inorganic substrates for preparation of the indicators. Silica pigment was found to be a particularly suitable inorganic substrate because of its wide utilisation as a polymer filler, low cost, ready availability, ease of handling, safety, and lack of colour (white). Indicators were prepared using both hydrophobic pigments (silica or alumina), and hydrophilic pigments (silica or alumina).

Titania was also used in connection with the preparation of oxygen-sensitive indicators. Titania was chosen because it is a semiconducting material which can act as a photocatalyst in the reduction and thus the activation of certain oxygen-sensitive dyes.

A variety of reactive dyes were employed to make the indicators. The choice of dye in each case was based upon the substance to be detected. The Tables presented in FIGS. 1, 2 and 3 show the dyes that were used in the preparation of carbon dioxide-sensitive indicators, ammonia-sensitive indicators, and oxygen-sensitive indicators, respectively.

Hydrophobic Silica or Alumina for $CO_2$ Indicators

Approximately 0.04 g of reactive dye was added to a beaker containing 2.0 g of hydrophobic silica (Degussa/Evonik Aerosil R812; S.S.A.=260+/−30 $m^2/g$; average particle size=7 nm) and approximately 100 mL of methanol. 1 mL of 1M tetrabutylammonium hydroxide in methanol was added. The mixture was well stirred/sonicated, the resulting solution was transferred to a round-bottomed flask and the methanol removed with the aid of a rotary evaporator at 30° C. under vacuum. The resultant powder was removed and ground into a fine powder using a pestle and mortar.

Pigments based on hydrophobic alumina (Degussa/Evonik Aeroxide Alu C805), rather than silica were also prepared as above and proved equally effective.

Alternative bases to tetrabutylammonium hydroxide can also used, including sodium hydroxide and sodium bicarbonate.

Alternative solvents to methanol can also be used, including ethanol and ethyl acetate.

Hydrophilic Silica or Alumina for $CO_2$ Indicators

Typically, a lower ratio of dye to inorganic pigment was used with hydrophilic silica (Degussa/Evonik Aerosil 300) and hydrophilic alumina (Degussa/Evonik Aeroxide Alu C).

To 15.0 g of hydrophilic silica (Degussa/Evonik Aerosil 300), 0.12 g of reactive dye was added. Approximately 100 mL water and 12 mL of 1.5 M tetrabutylammonium hydroxide in water was added. After stirring, the solvent (water) was evaporated under reduced pressure to produce to produce a fine powder.

Pigments based on hydrophilic alumina (Degussa/Evonik Aeroxide Alu C), rather than silica were also prepared as above and proved equally effective.

Hydrophobic Silica or Alumina for $NH_3$ Indicators

Approximately 1 g of reactive dye was added to a beaker containing 4.0 g of hydrophobic silica (Degussa/Evonik Aerosil R812; S.S.A.=260+/−30 $m^2$/g; average particle size=7 nm) and approximately 80 mL of methanol. The mixture was well stirred/sonicated, the resulting solution was transferred to a round-bottomed flask and the solvent removed with the aid of a rotary evaporator at 30° C. under vacuum. The resultant powder was removed and ground into a fine powder using a pestle and mortar.

Pigments based on hydrophobic alumina (Degussa/Evonik Aeroxide Alu C805), rather than silica were also prepared as above and proved equally effective.

Hydrophilic Silica or Alumina for $NH_3$ Indicators

Typically, a lower ratio of dye to inorganic pigment was used with hydrophilic silica (Degussa/Evonik Aerosil 300) and hydrophilic alumina (Degussa/Evonik Aeroxide Alu C).

Approximately 0.5 g of reactive dye was added to a beaker containing 4.0 g of hydrophilic silica (Degussa/Evonik Aerosil 300) and approximately 80 mL of water. The mixture was well stirred/sonicated, the resulting solution was transferred to a round-bottomed flask and the solvent (water) removed with the aid of a rotary evaporator at 30° C. under vacuum. The resultant powder was removed and ground into a fine powder using a pestle and mortar.

Pigments based on hydrophilic alumina (Degussa/Evonik Aeroxide Alu C), rather than silica were also prepared as above and proved equally effective.

Hydrophobic Silica or Alumina for Luminescence-Based $O_2$ Indicators

To 2.0 g of hydrophobic silica (Degussa/Evonik Aerosil R812, S.S.A.=260+/−30 $m^2$/g, average particle size=7 nm), 2 mg of an oxygen-sensitive luminescent dye, such as PtOEPK or Rudpp (tetraphenyl borate salt) was added in 100 mL of a suitable solvent (THF for PtOEPK or acetone for Rudpp). The mixture was mixed thoroughly and the solvent was removed under reduced pressure using a rotary evaporator. The resultant powder was removed and ground into a fine powder using a pestle and mortar.

Pigments based on hydrophobic alumina (Degussa/Evonik Aeroxide Alu C805), rather than silica were also prepared as above and proved equally effective.

Hydrophilic Silica or Alumina for Luminescence-Based $O_2$ Indicators

To 2.0 g of hydrophilic silica (Degussa/Evonik Aerosil 300), 2 mg of an oxygen-sensitive luminescent dye, such as Rudpp (chloride salt) was added in 100 mL of a polar solvent such as ethanol or water. The mixture was mixed thoroughly and the solvent was removed under reduced pressure using a rotary evaporator. The resultant powder was removed and ground into a fine powder using a pestle and mortar.

Pigments based on hydrophilic alumina (Degussa/Evonik Aeroxide Alu C), rather than silica were also prepared as above and proved equally effective.

Titania

Titania was used in connection with the preparation of certain oxygen-sensitive indicators. Titania was chosen because, in particular grades, it is a semiconducting material which can act as a photocatalyst in the reduction and thus the activation of certain oxygen-sensitive indicators. Because titania must be able to act as more than a support and drive the photoreduction of the dye to a form that is oxygen sensitive, the titania inorganic substrate was chosen in an untreated form so as to preserve its photocatalytic properties.

Solvent-Based Pigment for $O_2$ Indicators

To 2.0 g of titanium dioxide (Degussa/Evonik P25), 10 mg of reactive dye, 1.0 g of DL-Threitol and approximately 100 mL of ethanol were added. The mixture was mixed thoroughly and then the solvent (ethanol) removed under reduced pressure using a rotary evaporator. The resultant powder was removed and ground into a fine powder using a pestle and mortar.

Water-Based Pigment for $O_2$ Indicators

To 2.0 g of titanium dioxide (Degussa/Evonik P25), 10 mg of reactive dye, 1.0 g of DL-Threitol and approximately 100 mL of water were added. The mixture was mixed thoroughly and then the solvent (water) removed under reduced pressure using a rotary evaporator. The resultant powder was removed and ground into a fine powder using a pestle and mortar.

Incorporation in Polymer a) Hydrophobic Polymers

Polyethylene was chosen as a particularly suitable hydrophobic polymer due to its low cost, ease of manufacture and processability, and wide range of applications, including food packaging and medical applications.

In order to be compatible with polyethylene, the indicators used for incorporation into such polymer films were indicators based on hydrophobic silica, hydrophobic alumina, or untreated titania.

Typically 0.4 g of the hydrophobic indicator was added to 2.0-4.0 g of powdered polyethylene. The two powders were further ground until the colour was uniform. A small sample of the resulting powder was heat pressed at 115° C. for 5 minutes under 5 tonnes pressure using a Specac Atlas™ Series Heated Platens, before being allowed to cool. A 0.1 mm-thick plastic film was obtained.

This procedure is similar to that used in making extruded polymer films in which the pigment is dispersed, thus producing very thin polymer films.

Hydrophilic Polymers

Polyethylene oxide was chosen as a suitable hydrophilic polymer.

In order to be compatible with polyethylene oxide, the indicators used for incorporation into such polymer films were indicators based on hydrophilic silica, hydrophilic alumina, or untreated titania.

Typically 0.4 g of the hydrophilic indicator was added to 2.0-4.0 g of powdered polyethylene oxide. The two powders were further ground until the colour was uniform. A small sample of the resulting powder was heat pressed at 65° C. for 5 minutes under 5 tonnes pressure using a Specac Atlas™ Series Heated Platens, before being allowed to cool. A 0.1 mm-thick plastic film was obtained.

Results

Properties of Indicators a) Carbon Dioxide Indicators

The dyes listed in FIG. 1 were used as $CO_2$-sensitive reactive dyes for the preparation of the $CO_2$ indicators. The main dye used was m-Cresol Purple (MCP). The MCP-modified hydrophobic and hydrophilic silica pigments were prepared by the method described above and resulted in a fine blue powder.

Figure 5:
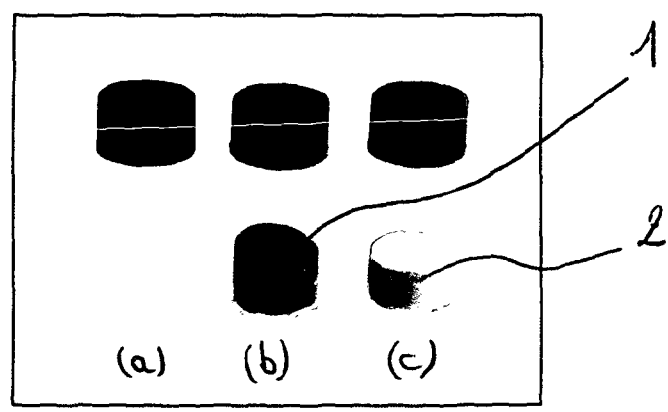
FIG. 5 A photograph representing the colour change of the $CO_2$-sensitive indicators of FIG. 4, and showing (a) untreated silica, (b) MCP-modified silica pigments prior to exposure to carbon dioxide, and (c) MCP-modified silica pigments after exposure to carbon dioxide.
Figure 6:
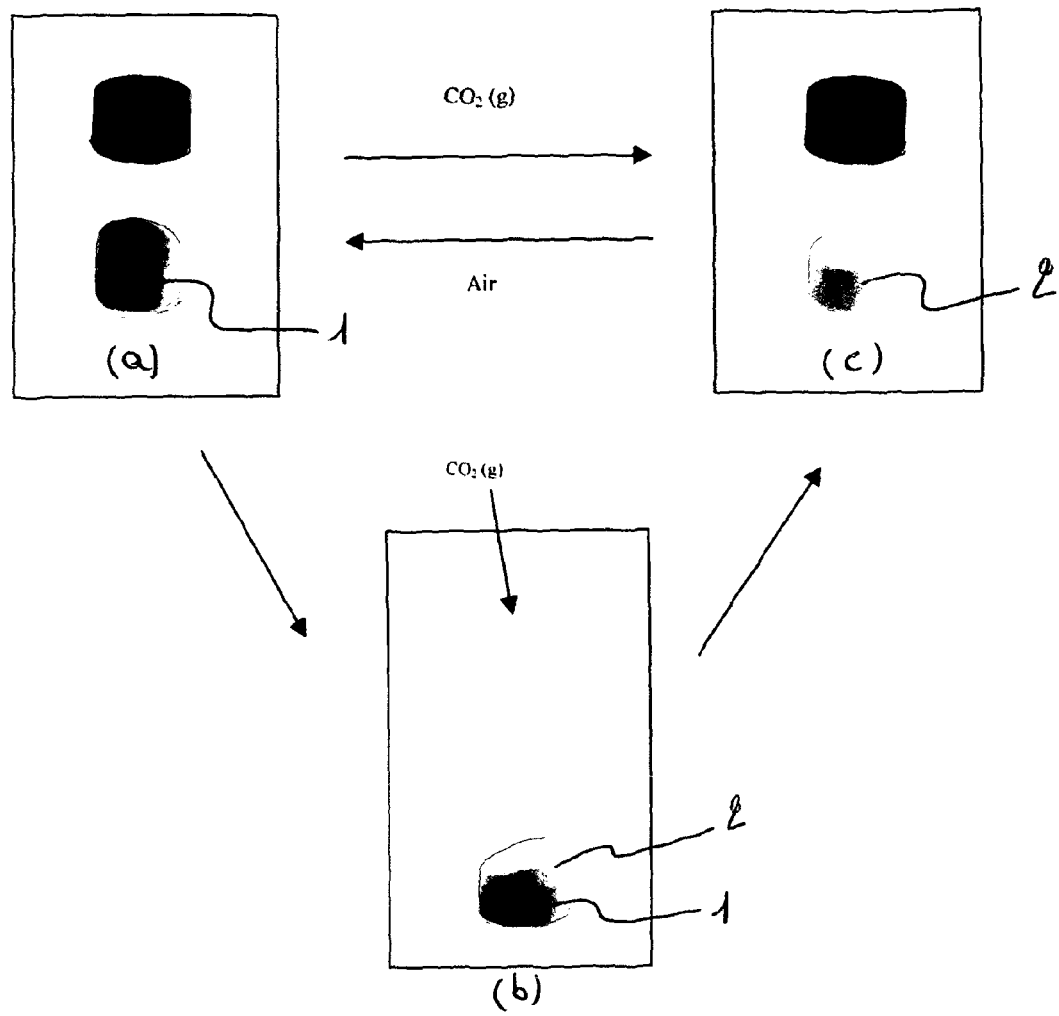
FIG. 6 A photograph representing the colour change of the $CO_2$-sensitive indicators of FIG. 4, and showing (a) MCP-modified silica pigments prior to exposure to carbon dioxide, (b) MCP-modified silica pigments during exposure to carbon dioxide, and (c) MCP-modified silica pigments after exposure to carbon dioxide.

As shown in FIGS. 4, 5 and 6, the bright blue 1 pigment immediately turned into bright yellow 2 upon exposure to carbon dioxide gas. The colour change was fully reversible. The pigment gradually returned to its original blue 1 colour as the concentration of carbon dioxide decreased.

Colour change of MCP-modified silica pigments was also observed on a particle scale under the microscope using an Olympus SZ11 microscope, fitted with a DP12 digital camera, for indicators based on both hydrophobic and hydrophilic silica pigments. In the case of hydrophilic silica crystals being used (average crystal size approximately 100 µm), magnification at ×220 showed colour change of single crystals very clearly. The crystals of the hydrophobic silica pigment are significantly smaller, so the colour change in individual crystals was not visible at this magnification. However, clear colour change of the overall crystalline matrix was observed.

The indicators were found to be very stable, with no loss in performance even after 8 months stored in a glass jar. This was unexpected, as it could not have been predicted that coating or impregnating reactive dyes such as MCP onto silica pigments would significantly improve the stability of such dyes.

Figure 7:
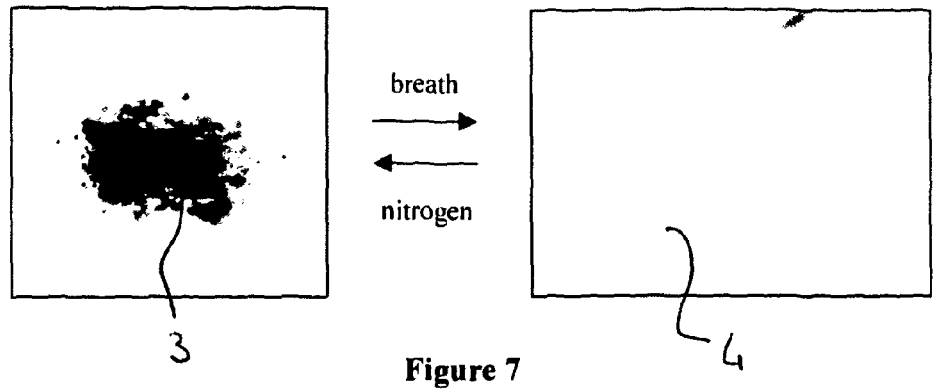
FIG. 7 A photograph showing the colour change of $CO_2$-sensitive indicators according to a first embodiment of an aspect of the present invention when exposed upon carbon dioxide in human breath, using thymolphthalein as reactive dye.
Figure 8:
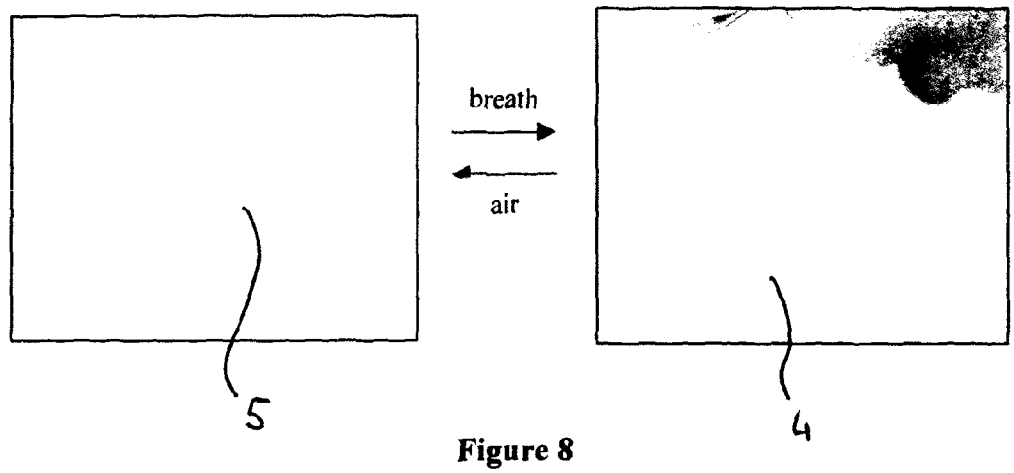
FIG. 8 A photograph showing the colour change of $CO_2$-sensitive indicators according to a first embodiment of an aspect of the present invention when exposed upon carbon dioxide in human breath, using o-cresolphthalein as reactive dye.

FIGS. 7 and 8 depict alternative embodiments of the $CO_2$-sensitive pigments, and show the effect of breath activation on such indicators.

The indicator shown in FIG. 7 was a based on a hydrophobic silica pigment modified with thymolphthalein. The bright blue 3 pigment immediately turned colourless 4 upon exposure to carbon dioxide contained in human breath (typically 5%). The colour change was fully reversible. The pigment gradually returned to its original blue 3 colour upon purging under nitrogen.

The indicator shown in FIG. 8 was a based on a hydrophobic silica pigment modified with o-cresolphthalein. The purple 5 pigment immediately turned colourless 4 upon exposure to carbon dioxide contained in human breath. The colour change was fully reversible. The pigment gradually returned to its original purple 5 colour under normal atmosphere.

b) Ammonia Indicators

The dyes listed in FIG. 2 were used as $NH_3$-sensitive reactive dyes for the preparation of the ammonia indicators. All these dyes, with the exception of Phloxine B (PB), are hydroxytriarylmethane dyes, and more specifically, sulfonphthaleins. These are typically pH indicator dyes which, when placed in a sufficiently basic environment, undergo deprotonation. Such deprotonation results in a shift in the maximum wavelength on the absorption spectrum ($\lambda_{max}$).

The main dye used was Bromophenol Blue, (BPB), the structure of which is shown below:

The ammonia indicators thus prepared were exposed to the headspace from a 25% ammonia solution.

Figure 9:
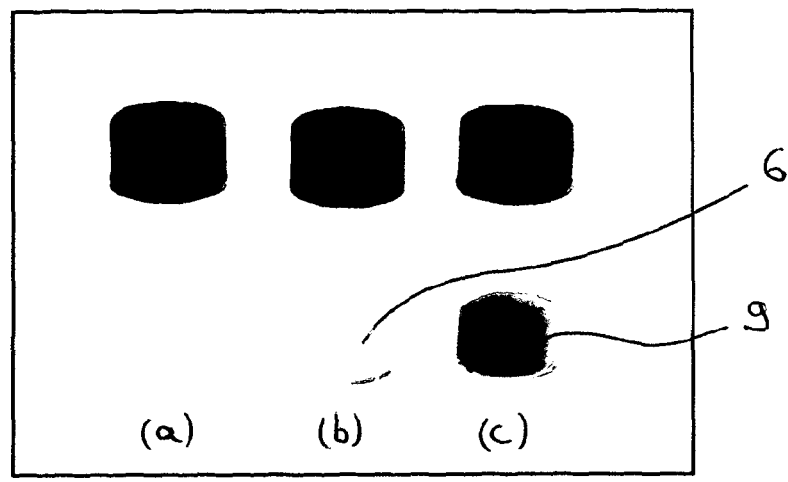
FIG. 9 A photograph representing the colour change of ammonia-sensitive indicators according to a second embodiment of an aspect of the present invention, and showing (a) untreated silica, (b) BPB-modified silica pigments prior to exposure to ammonia, and (c) BPB-modified silica pigments after exposure to ammonia gas.
Figure 10:
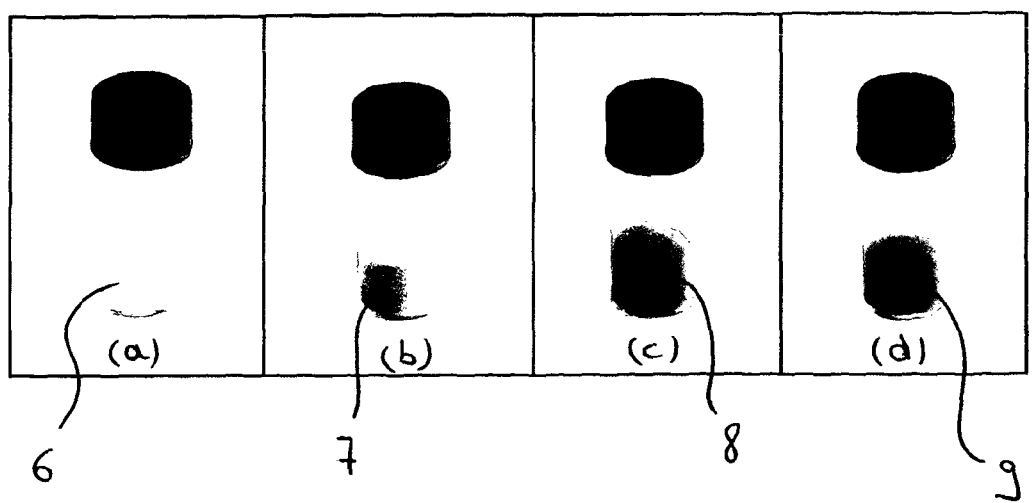
FIG. 10 A photograph representing the colour change of the ammonia-sensitive prior to exposure to ammonia, and (b), (c) and (d) BPB-modified silica pigments upon increasing exposure to ammonia gas.

As shown in FIGS. 9 and 10, the bright orange 6 pigment turned into ochre 7, green 8, and finally blue 9 upon increasing exposure to ammonia gas.

Colour change of BPB-modified silica pigments was also observed on a particle scale under the microscope using an Olympus SZ11 microscope, fitted with a DP12 digital camera, for indicators based on both hydrophobic and hydrophilic silica pigments. In the case of hydrophilic silica crystals being used (average crystal size approximately 100 µm), magnification at ×220 showed colour change of single crystals very clearly. The crystals of the hydrophobic silica pigment are significantly smaller, so the colour change in individual crystals was not visible at this magnification. However, clear colour change of the overall crystalline matrix was observed.

The indicators were found to be very stable, with no loss in performance even after 6 months stored in a glass jar. This was unexpected, as it could not have been predicted that coating or impregnating reactive dyes such as BPB onto silica pigments would significantly improve the stability of such dyes.

c) Oxygen Indicators

The dyes listed in FIG. 3 were used as $O_2$-sensitive reactive dyes for the preparation of the oxygen indicators. The oxygen indicators were either luminescence based or colorimetric based.

The main colorimetric oxygen-sensitive dye used was MB. The MB-modified titania pigments were prepared by the method described above and resulted in a fine blue powder.

Colour change of MB-modified titania pigments was observed on a particle scale under the microscope using an Olympus SZ11 microscope, fitted with a DP12 digital camera. FIG. 11 relates to a solvent-based $MB/TiO_2$/DL-Threitol pigment, whereas FIG. 12 relates to a water-based $MB/TiO_2$/DL-Threitol pigment.

As shown in FIGS. 11 and 12, the bright blue 14 pigments turned colourless 15 upon exposure to UVA radiation for approximately 1 minute. The colour change was fully reversible upon exposure to oxygen in air. The pigments gradually returned to their original blue 14 colour as the dye was re-oxidised by gaseous oxygen.

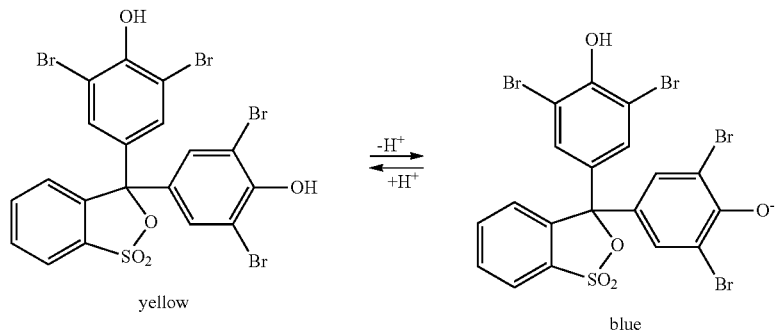

BPB has a p$K_a$ of 4.10 and undergoes a shift in $\lambda_{max}$ from 430 nm in its yellow acidic form to 600 nm in its blue basic form.

The BPB-modified hydrophobic and hydrophilic silica pigments were prepared by the method described above and resulted in a fine orange powder.

The main luminescence-based oxygen-sensitive dye used was Rudpp, which was rendered solvent soluble by ion-pairing with a lipophilic counterion, such as tetraphenyl borate.

The indicators were found to be very stable, with no loss in performance even after 12 months stored in a glass jar. This was unexpected, as it could not have been predicted that coating or impregnating reactive dyes such as Rudpp or MB onto silica pigments would significantly improve the stability of such dyes.

Properties of Polymer Films

The incorporation of the indicators in polymer films such as polyethylene films signifies the ability to make extruded polymer films, with sensing properties. However, it was not clear whether the notably unstable reactive dyes upon which the indicators are based would be able to withstand incorporation into a polymer, and subsequent processing of the polymer composite via known methods.

a) Carbon Dioxide Indicators

MCP-modified hydrophobic silica pigments were incorporated into polyethylene by the method described above. An approximately 0.1 mm-thick blue plastic film was obtained. The film was exposed to carbon dioxide gas, and the resulting colour change was observed.

Figure 13:
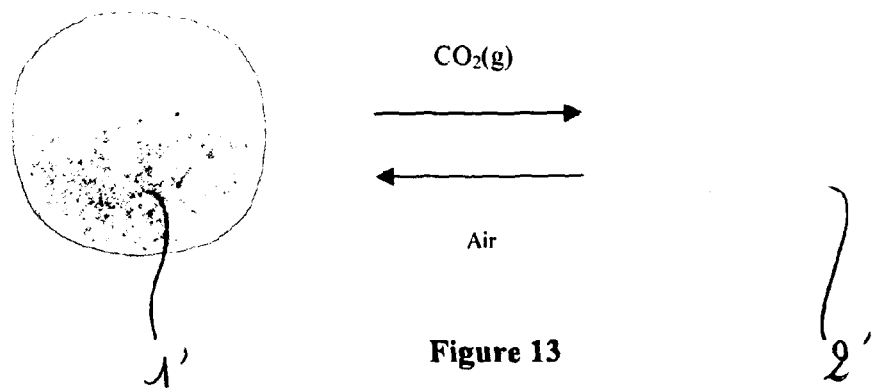
FIG. 13 A photograph showing the colour change of a $CO_2$-sensitive polymer composite film according to a first embodiment of an aspect of the present invention when exposed to carbon dioxide, using the indicator of FIG. 4.

As shown in FIG. 13, the blue 1' film turned into yellow 2' upon exposure to carbon dioxide gas. The colour change was fully reversible. The film gradually returned to its original blue 1 colour as the concentration of carbon dioxide decreased.

Figure 14:
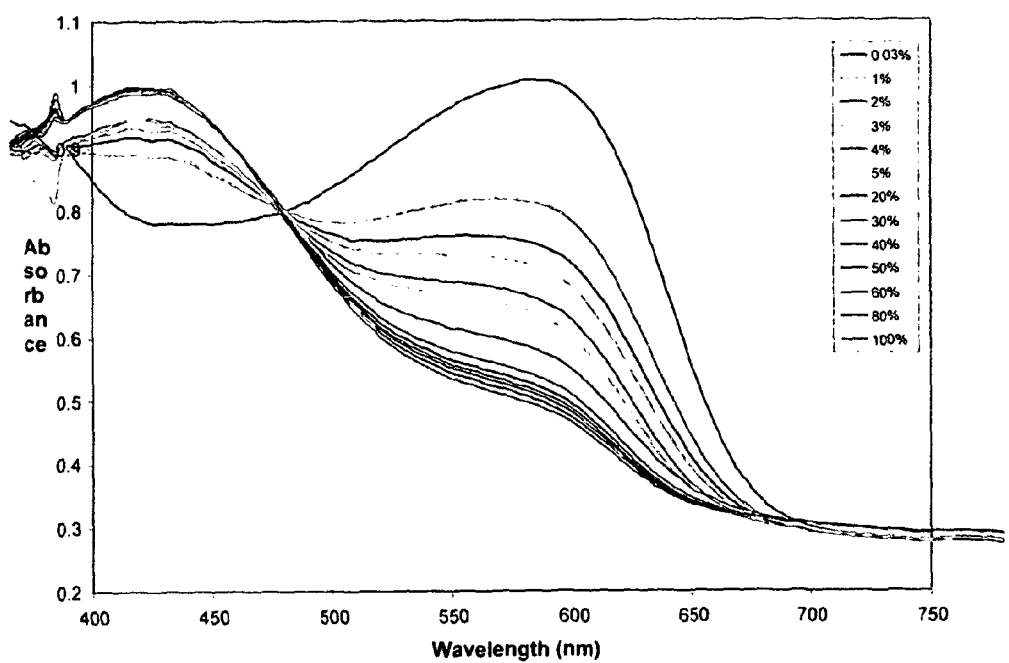
FIG. 14 A recorded UV-visible spectrum of the $CO_2$-sensitive polymer composite film of FIG. 13, as a function of carbon dioxide concentration.

As shown in FIG. 14, the maximum absorption wavelength of the plastic film was a function of % CO, in the surrounding atmosphere. It can be seen that, as the dye changed from its deprotonated form to its protonated form, the maximum absorption wavelength shifted from 592 to 424 nm. Importantly, the sensitivity of such plastic films was found to be excellent. As shown in FIG. 14, the maximum absorption wavelength shifted from 592 to 424 nm in an environment containing as low as 2% $CO_2$.

Figure 15:
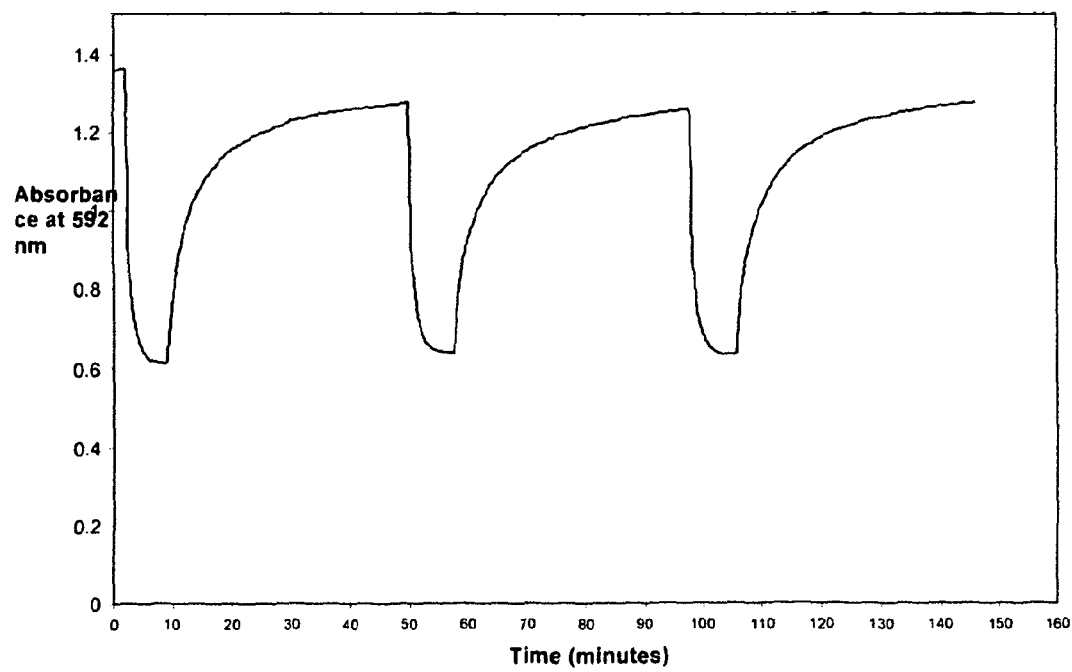
FIG. 15 An absorbance response at 592 nm of the $CO_2$-sensitive polymer composite film of FIG. 13, showing three cycles of response to 100% carbon dioxide followed by air purge recovery.

Repeatability was investigated by exposing the films to 100% $CO_2$, then purging with air. 100% $CO_2$ was chosen for this set of experiments because response of the plastic film indicators was faster than when using lower concentrations of $CO_2$. As illustrated in FIG. 15, the performance of the $CO_2$-sensitive plastic film indicators was found to be intact after 3 cycles of exposure to carbon dioxide and air purges, with both sensitivity and recovery unaffected.

b) Ammonia Indicators

BPB-modified hydrophobic silica pigments were incorporated into polyethylene by the method described above. An approximately 0.1 mm-thick orangy yellow plastic film was obtained. The films were exposed to 1000 ppm ammonia gas in nitrogen, and the resulting colour changes were observed.

Figure 16:
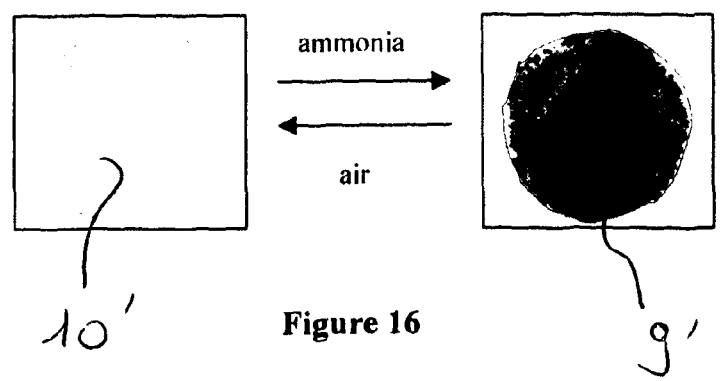
FIG. 16 A photograph showing the colour change of an ammonia-sensitive polymer composite film according to a second embodiment of an aspect of the present invention when exposed to 1000 ppm ammonia in nitrogen, using the indicator of FIG. 9.

As shown in FIG. 16, the orangy yellow 10' film turned into blue 9' upon exposure to ammonia gas. The colour change was fully reversible.

Figure 17:
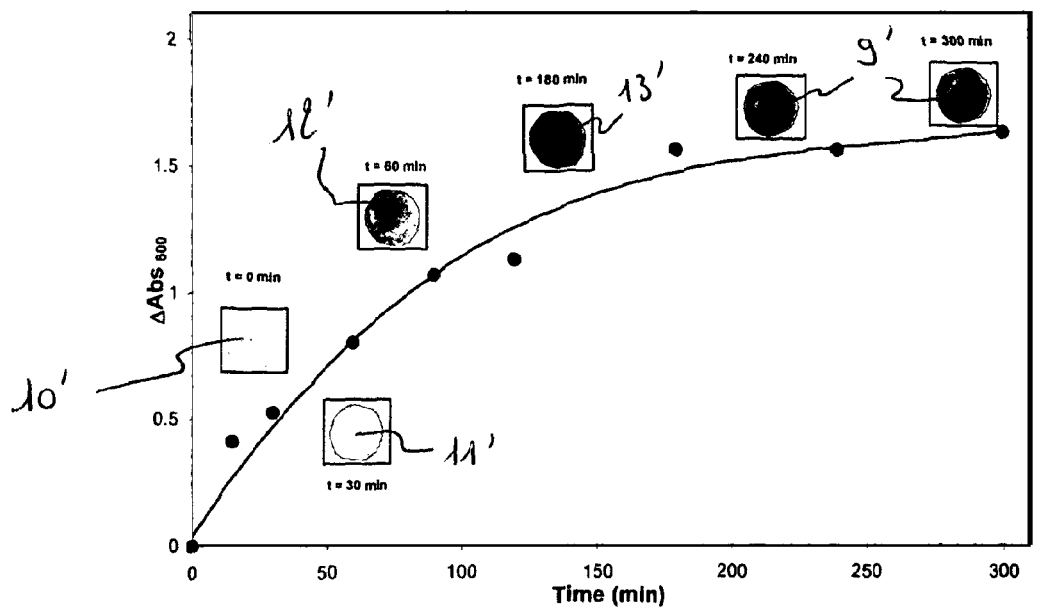
FIG. 17 An absorbance response at 600 nm versus time of the ammonia-sensitive polymer composite film of FIG. 16 under 1000 ppm ammonia in nitrogen.

The colour change observed under such conditions was gradual, as illustrated in FIG. 17. The film gradually turned from orangy yellow 10' to light green 11', blue-green 12', dark blue-green 13', and finally blue 9'.

Figure 18:
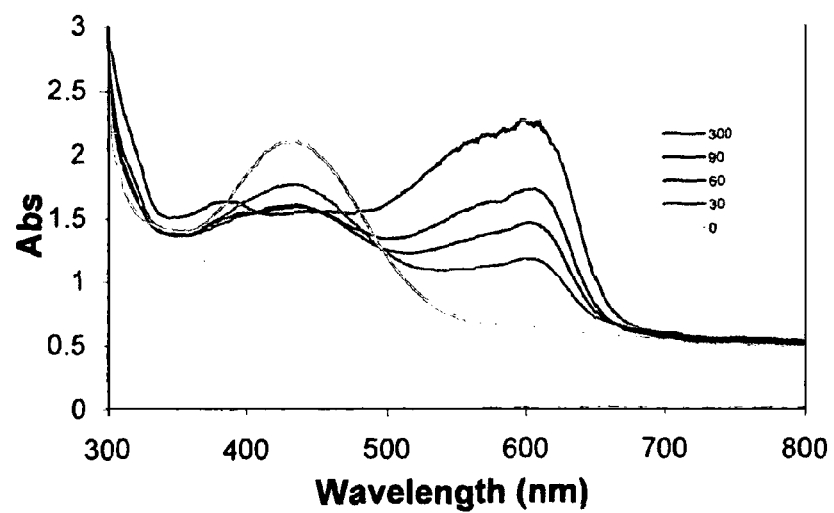
FIG. 18 A recorded UV-visible spectrum of the ammonia-sensitive polymer composite film of FIG. 16, as a function of exposure time to 1000 ppm ammonia in nitrogen.

As shown in FIG. 18, the maximum absorption wavelength of the plastic film was a function of exposure time to ammonia in the surrounding atmosphere. It can be seen that, as the dye changed from its first chemical form to its second chemical form, the maximum absorption wavelength shifted from approximately 420 to approximately 600 nm.

The BPB-based ammonia-sensitive plastic film indicators were found to recover slowly under ambient conditions, even with additional nitrogen purges. However, the recovery period was found to be greatly shortened by heating films at approximately 70° C. As illustrated in FIG. 19, the performance of the BPB-based ammonia-sensitive plastic film indicators was found to be intact after 5 cycles of exposure to ammonia and thermal recovery, with both sensitivity and recovery unaffected.

Further investigation was carried out for all seven ammonia-sensitive reactive dyes listed in FIG. 2. Films were tested with 1000 ppm ammonia in nitrogen with a 1 hour exposure time. A comparison of the response and recovery characteristics is shown in the Table provided in FIG. 20. It can be observed that the use of different reactive dyes in the indicators pigments provided in the corresponding ammonia-sensing plastic films leads to varied response to exposure to ammonia gas and recovery under ambient conditions. Therefore, the use of a particular type of dye may be tailored to the application envisaged for the corresponding indicator. For example, in food packaging, the release of volatile amines by decaying food is a slow and gradual process, therefore a moderately fast but clearly visible response is likely to be satisfactory. However, in other applications such as monitoring of a chemical environment, e.g., in a laboratory, fast response is likely to be a crucial parameter.

c) Oxygen Indicators

MB-modified titania pigments were incorporated into polyethylene by the method described above. An approximately 0.1 mm-thick blue plastic film was obtained. The film was bleached upon irradiation with UV light under nitrogen for approximately 1 minute. It was then exposed to oxygen gas, and the resulting colour recovery was observed.

Figure 21:
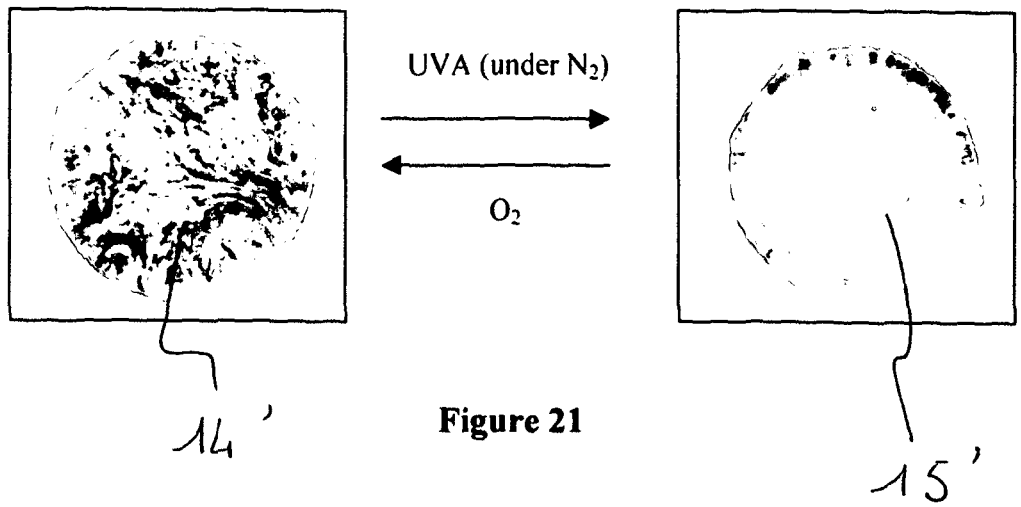
FIG. 21 A photograph showing the colour change of an oxygen-sensitive polymer composite film according to a third embodiment of an aspect of the present invention when exposed to oxygen, using the indicator of FIG. 11.
Figure 22:
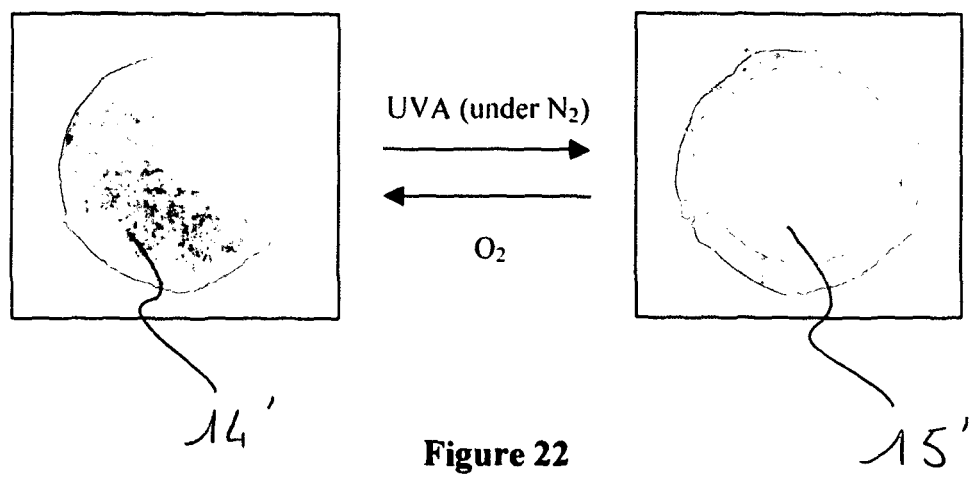
FIG. 22 A photograph showing the colour change of an oxygen-sensitive polymer composite film according to a third embodiment of an aspect of the present invention when exposed to oxygen, using the indicator of FIG. 12.

FIG. 21 relates to a solvent-based $MB/TiO_2$/DL-Threitol pigment in polyethylene, whereas FIG. 22 relates to a water-based $MB/TiO_2$/DL-Threitol pigment in polyethylene oxide.

As shown in FIGS. 21 and 22, the blue 14' film turned colourless 15' upon exposure to UVA light under nitrogen for approximately 4 to 5 minutes. The colour change was fully reversible upon exposure to oxygen in air. The films gradually returned to their original blue 14' colour the dye was re-oxidised by gaseous oxygen.

A typical luminescence based indicator plastic film (not shown), using a Rudpp-modified titania pigment, was also tested. The film exhibited decreasing luminescence with increasing level of oxygen.

The invention claimed is:

1. A polymer composite comprising at least one thermoplastic polymer, and at least one chemical indicator dispersed in the at least one thermoplastic polymer, the at least one chemical indicator comprising a particulate inorganic substrate, and at least one reactive dye or ink coated on and/or impregnated within the particulate inorganic substrate.

2. The polymer composite according to claim 1, wherein the at least one chemical indicator is substantially uniformly dispersed in the at least one thermoplastic polymer.

3. The polymer composite according to claim 1, wherein the polymer composite is melt-processed in the form of a film, sheet, or tube.

4. The polymer composite according to claim 1, wherein the chemical indicator has a thermal stability of at least 80° C.

5. The polymer composite according to claim 4, wherein the chemical indicator has a thermal stability of at least 110° C.

6. The polymer composite according to claim 1, wherein the at least one thermoplastic polymer comprises an addition polymer.

7. The polymer composite according to claim 6, wherein the addition polymer is a polyolefin.

8. The polymer composite according to claim 7, wherein the polyolefin is polyethylene.

9. The polymer composite according to claim 6, wherein the addition polymer is polystyrene.

10. The polymer composite according to claim 1, wherein the at least one thermoplastic polymer comprises a condensation polymer.

11. The polymer composite according to claim 10, wherein the condensation polymer is selected from the group consisting of a polycarbonate, polyether, polyester, polyamide and/or polyacetal.

12. The polymer composite according to claim 1, wherein the at least one thermoplastic polymer comprises a hydrophobic polymer, and the at least one chemical indicator comprises a hydrophobic particulate inorganic substrate or an untreated particulate inorganic substrate.

13. The polymer composite according to claim 1, wherein the at least one thermoplastic polymer comprises a hydrophilic polymer, and the at least one chemical indicator comprises a hydrophilic particulate inorganic substrate or an untreated particulate inorganic substrate.

14. A method of manufacturing a polymer composite according to claim 1, comprising dispersing in at least one thermoplastic polymer at least one chemical indicator comprising a particulate inorganic substrate and at least one reactive dye or ink coated on and/or impregnated within the particulate inorganic substrate.

15. The method according to claim 14, comprising grinding the at least one polymer and the at least one chemical indicator.

16. The method according to claim 14, comprising fabricating the polymer composite by melt-processing, extruding, and/or moulding.

17. The method according to claim 16, comprising blending a plurality of said polymer composites prior to or during fabrication, each polymer composite being capable of detecting the presence of one or more selected analytes.

18. The polymer composite according to claim 1 comprised with an item of food packaging, a medical device, a carbon dioxide sensor or indicator, an ammonia sensor or indicator, or an oxygen sensor or indicator.

19. The polymer composite according to claim 1, wherein the chemical indicator has a storage stability under dark, ambient conditions, of at least one week.

20. The polymer composite according to claim 10, wherein the chemical indicator has a storage stability under dark, ambient conditions, of at least one month.

21. The polymer composite according to claim 19, wherein the chemical indicator has a storage stability under dark, ambient conditions, of at least six months.

22. The polymer composite according to claim 1, wherein the indicator comprises a colourimetric or luminescence-based indicator.

23. The polymer composite according to claim 1, wherein the particulate inorganic substrate is in powder form.

24. The polymer composite according to claim 1, wherein the particulate inorganic substrate comprises an inorganic pigment selected from silica, titania, alumina, magnesium oxide, calcium oxide or a zeolite.

25. The polymer composite according to claim 1, wherein the at least one reactive dye comprises a carbon dioxide-sensitive reactive dye selected from the list consisting of m-Cresol Purple (MCP, Hydroxy triarylmethane), Thymolphthalein (3,3-bis(4-hydroxy-2-methyl-5-propan-2-ylphenyl)-2-benzofuran-1-one), o-Cresolphthalein, Acryloly florescein (AcFl),β-methyl umbelliferon (BMUB), Bromothymol blue (BTB, Hydroxy triarylmethane), 5' and 6'-Carboxyseminaphtholfluorescein (c-SNAFL), 5' and 6'-Carboxyseminaphtholrhodamine (c-SNARF), Cresol Red (CR, o-Cresolsulfonephthalein), Hexadecyl trimethyl ammonium cation ($CTA^+$), Hexadecyl trimethyl ammonium hydroxide (CTAH), Dual lumophore referencing (DLR), 2-(2,4-Dinitrophenylaxo)-1-naphthol-3,6disulphonic acid (DNPA), tris(thenoyltrifluoroacetonato) europium (III) ([Eu$(tta)_3$]), Fluorescein (Fl, resorcinolphthalein), 7-hydroxycoumarin-4-acetic acid (HCA), 1, Hydroxypyrene-3,6,8-trisulphonic acid (HPTS), Neutral red (NR, toluylene red), Phenol Red (PR, phenolsulfonphthalein), Rhodamine 6G (R6G), Sulforhodamine 101 (SRh), Thymol blue (TB, thymolsulphonephthalein), and/or Texas Red hydrazine (THR).

26. The polymer composite according to claim 1, wherein the at least one reactive dye comprises an ammonia-sensitive reactive dye selected from the list consisting of Bromophenol Blue (BPB, Hydroxy triarylmethane), Bromocresol Green (BCG, Hydroxy triarylmethane), Bromocresol Purple (BCP, Hydroxy triarylmethane), Bromothymol Blue (BTB, Hydroxy triarylmethane), Phloxine Blue (PB, Fluorone), Thymol Blue (TB, Hydroxy triarylmethane), and/or m-Cresol Purple (MCP, Hydroxy triarylmethane).

27. The polymer composite according to claim 1, wherein the at least one reactive dye comprises an oxygen-sensitive reactive dye selected from the list consisting of Methylene blue (MB, thiazine), Thionine (Th, thiazine), Azure B (AzB, thiazine), Nile blue (NR, oxazine), Ruthenium tris bypyridyl (Rubpp, metal complex), tris(4,7-diphenyl-1,10-phenanthroline) ruthenium (II) perchlorate (Rudpp, metal complex), Platinum (II) octaethyl porphyrin ketone (PtOEPK, metal complex), and/or Proflavin (Pf, proflavin), or a dye which exhibits a fluorescence that is quenched by oxygen selected from the list consisting of ruthenium (II) trisbypyridine dichloride or Platinum tetraoctylpyridyl porphyrin.

28. The polymer composite according to claim 1, wherein the chemical indicator comprises more than one reactive dye.

* * * * *

UNITED STATES PATENT AND TRADEMARK OFFICE
CERTIFICATE OF CORRECTION

| | | |
|---|---|---|
| PATENT NO. | : 8,790,930 B2 | Page 1 of 1 |
| APPLICATION NO. | : 13/502268 | |
| DATED | : July 29, 2014 | |
| INVENTOR(S) | : Mills et al. | |

It is certified that error appears in the above-identified patent and that said Letters Patent is hereby corrected as shown below:

In the Claims

Column 17,
Line 39, "claim 10" should read --claim 19--.

Signed and Sealed this
Sixteenth Day of December, 2014

Michelle K. Lee
*Deputy Director of the United States Patent and Trademark Office*